United States Patent [19]
Mahoney et al.

[11] Patent Number: 5,443,698
[45] Date of Patent: Aug. 22, 1995

[54] ELECTROSYNTHESIS OF METAL CARBOXYLATES

[75] Inventors: Dennis M. Mahoney, Long Valley; George S. Mossaad, So. Toms River, both of N.J.

[73] Assignee: Hüls America Inc., Piscataway, N.J.

[21] Appl. No.: 238,955

[22] Filed: May 6, 1994

[51] Int. Cl.$^6$ .............................................. C25B 3/12
[52] U.S. Cl. .............................. 204/59 QM; 204/86
[58] Field of Search ......................... 204/59 QM, 86

[56] References Cited

U.S. PATENT DOCUMENTS 4,416,743 11/1983 Holland ........................... 204/59 M Primary Examiner—John Niebling
Assistant Examiner—Edna Wong
Attorney, Agent, or Firm—Davis Hoxie Faithfull & Hapgood

[57] ABSTRACT

The invention relates to a method of synthesizing a metal carboxylate comprising:

(a) placing an anode and a cathode in contact with an emulsion, wherein said anode includes a metal which, during electrolysis, reacts with a carboxylic acid to form a metal carboxylate, wherein the cathode comprises a material inert to the electrolytic reaction, and the emulsion comprises a carboxylic acid, an aqueous phase which includes an electrolyte, and an organic phase; and, (b) passing a current between the anode and cathode to effect an electrolytic reaction between the metal of the anode and the carboxylic acid to form the metal carboxylate.

20 Claims, 4 Drawing Sheets

ELECTROSYNTHESIS OF METAL CARBOXYLATES

BACKGROUND OF THE INVENTION

The present invention relates to the electrosynthesis of metal carboxylates. In the conventional thermal batch method of synthesizing metal carboxylates, a fine powder of the metal is suspended in an organic solvent which includes an organic acid. Reaction is effected by heating the mixture at elevated temperatures for a predetermined period of time. In another known method, a halide salt of the metal is dissolved in an aqueous solution containing an alkali metal carboxylate, and the metal carboxylate precipitates out of solution.

Electrosynthesis of metal carboxylates is known, but the use of an emulsion in such a process is not. International application number PCT/GB85/00054, published Aug. 15, 1985 under Publication No. WO 85/03530, discloses the preparation of heavy metal carboxylates through an electrolytic method. The publication states that an electric current is passed through an anode comprising a heavy metal and an inert cathode in an aqueous electrolyte containing at least one carboxylic acid. A heavy metal carboxylate results. The PCT application discloses that the carboxylic acid can be miscible in the aqueous solution, immiscible in the solution, or insoluble in the solution. In the case where the acid is immiscible, the application does not disclose or suggest the use of an emulsion but, rather, indicates that the acid itself can be a liquid layer separate from the aqueous solution.

Unlike the use of a separate layer of an immiscible carboxylic acid, the use of an emulsion, in accord with the present invention, offers several advantages. First, faster reaction times result because an emulsion provides greater surface area for reaction between the metal and the carboxylic acid. Second, a clean product results because of the selective extraction of the metal carboxylate into the organic phase. These two advantages are the unexpected result of the interfacial equilibrium between the organic suspension within the aqueous solution.

The metal carboxylates produced according to the invention described and claimed herein generally can be classified as metallic soaps. Metallic soaps are a group of water insoluble compounds containing alkaline earth or heavy metals combined with monobasic carboxylic acids. Metallic soaps are classified as acid soaps containing free acid (positive acid number), neutral soaps containing no free acid (zero acid number), or basic soaps which are characterized by a higher metal-to-acid equivalent ratio than the stoichiometric amount. Metallic soaps can be used as, among other things, stabilizers for plastics, fungicides, catalysts, driers, and fuel additives. The most important group of the metallic soaps are the "driers" which promote and accelerate the drying, curing, or hardening of oxidizable coating vehicles such as paints.

SUMMARY OF THE INVENTION

The present invention provides an electrosynthetic method of producing metal carboxylates. In the method of the invention, an electric current is passed through an anode comprising the chosen metal and a cathode comprising an inert material. The current passes between each electrode through an aqueous emulsion comprising a carboxylic acid, an organic phase and an aqueous phase containing an electrolyte. The applied current can be an AC or a DC current.

DETAILED DESCRIPTION OF THE INVENTION

Figure 1:
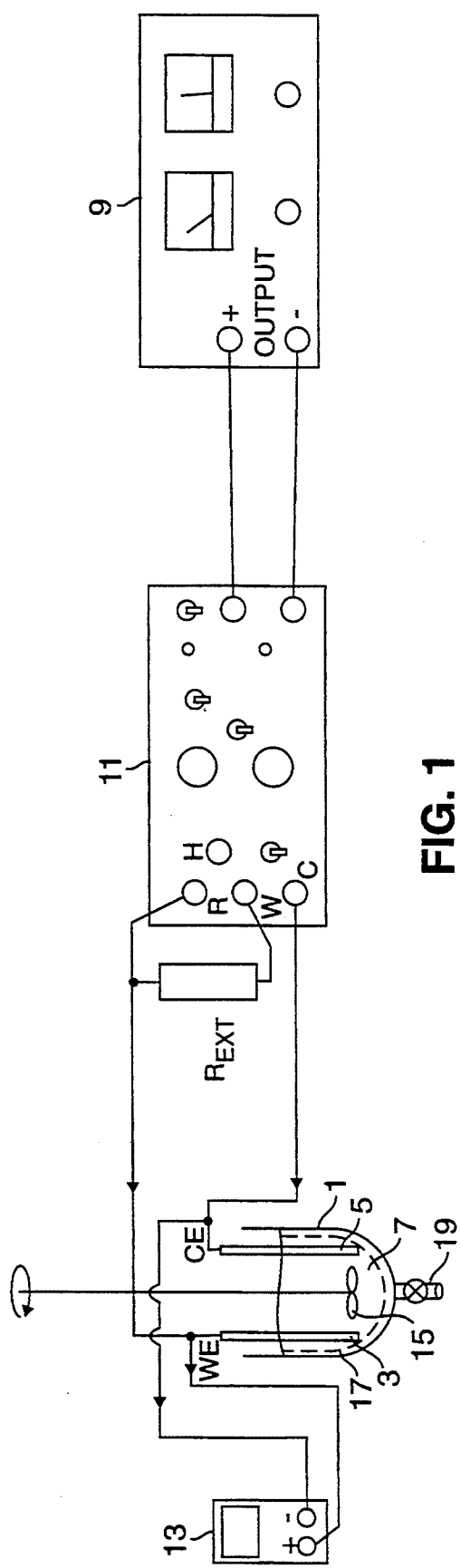
FIG. 1 is a diagram showing an electrolytic cell connected to an electronic power supply.

In accord with the method of the present invention, metal carboxylates are produced by an electrosynthetic process. FIG. 1 shows a cell 1 in which the synthesis can be effected. The cell comprises an anode 3 and a cathode 5, and an emulsion 7 in which each electrode is inserted. The power supply 9 can be a DC power supply, model 420, from the Electrosynthesis Co., New York. The potentiostatic controller 11 contains the current and potential control electronic circuitry necessary for the application of power to an electrochemical process. The controller illustrated is the model 410 potentiostat, which is also sold by the Electrosynthesis Co. The digital coulometer 13 provides a direct readout of the number of coulombs charged to the electrosynthetic process. The coulometer illustrated is a model 640 from the Electrosynthesis Co. The mechanical stirrer 15 provides agitation to the reaction medium which generally increases the rate of reaction and maintains the emulsion.

The anode 3 is consumed in the course of the synthesis. The anode 3 comprises the metal which forms the metal carboxylate. The anode can be manufactured from any suitable metal including, but not limited to, iron, cobalt, copper, aluminum, titanium, vanadium, zirconium, molybdenum, silver, gold, and nickel. While alloys can be used, the metal carboxylate produced will include a mixture of the different alloy metals, and the ratio of the metals in the resulting carboxylate will depend on the electrochemical potentials of the different alloy metals. Example XVI, described below, illustrates the result that can be expected when the anode comprises an alloy. The cathode can be manufactured from any suitable electrolytically inert material including, but not limited to, platinum, stainless steel and graphite. In addition to comprising a solid metal, the cathode can take other suitable forms, such as a gas diffusion cell.

The current applied in accord with the present invention can comprise a DC or an AC current. With the application of a DC current, the following reaction sequence (I) occurs:

$$\text{Anode } M° \rightarrow M^{+2} + 2e^- \quad \quad (I)$$

$$\text{Cathode } 2e^- + 2H_2O \rightarrow H_2 + 2OH^-$$

$$2OH^- + 2RCOOH \rightarrow 2H_2O + 2RCOO^-$$

$$\text{Total Reaction: } M° + 2RCOOH \rightarrow M(RCOO)_2 + H_2$$

In the emulsion medium described herein, the reaction sequence (I) can be illustrated as follows:

| Organic Phase | 2RCOOH | (RCOO$^-$)$_2$M$^{+2}$ |
|---|---|---|
| | ↓ | ↑ |
| Aqueous Phase | 2(RCOO$^-$) + M$^{+2}$ | →(RCOO$^-$)$_2$M$^{+2}$ |

As shown, the metal carboxylate of interest ultimately migrates to, and is extracted from, the organic phase.

The emulsion used according to the method of the present invention includes one or more carboxylic acids. Acids which can be used include, but are not limited to, 2-ethylhexanoic, naphthionic, oleic, lauric, palmitic, phthalic, acetic, gluconic and neodecanoic acids. Other acids indicated as useful in International application number PCT/GB85/00054 can also be used. The organic phase includes one or more organic components which form an organic phase distinct from the aqueous phase. Such components typically are not soluble, or have limited solubility, in the aqueous phase. Organic components include, but are not limited to, mineral spirits, heptane, hexane, and petroleum ether. The electrolyte which provides adequate current through the emulsion can be any suitable organic or inorganic salt including, but not limited to, sodium hydroxide, tetraethylammonium chloride, tetraethylammonium iodide, sodium chloride, ammonium acetate, tetrabutyl ammonium perchlorate, tetraethyl ammonium bromide, and tetraethyl ammonium p-toluene sulfonate, at concentrations ranging from 0.02 to 1.5N. While concentrations in excess of 1.5N can be used, the process may produce heavy cathode plating and a relative increase in the metal concentration in the aqueous phase.

The various parameters associated with the method of the present invention can be varied to optimize the overall reaction scheme. While the following discussion is generally directed to the preparation of any metal carboxylate, specific reference is made to the preparation of cobalt octoate. The specific preparation referred to was carried out in a cell design similar to that illustrated in FIG. 1. The electrodes consisted of a cobalt anode and a electrolytically inert cathode. The emulsion included 2-ethylhexanoic acid, with the organic phase comprising mineral spirits.

In the method of the present invention, the electroactive area per unit reactor volume should be high. Adequate heat transfer should be available between the reactor and its environment. The cost of the electrolysis will be minimized with the use of low cell voltage, small interelectrode gap, and an appropriate electrolyte to provide adequate electrolytic conductivity.

Figure 2:
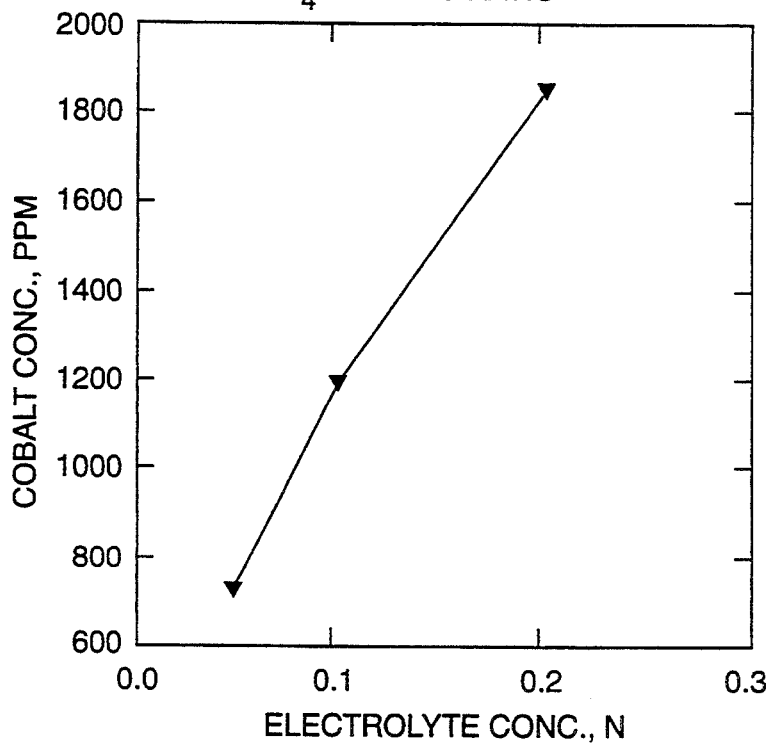
FIG. 2 is a graph showing the relationship between electrolyte concentration and concentration of cobalt in the aqueous phase.

In the preparation of cobalt octoate, selection of the right electrolyte at an appropriate concentration has lowered the cell voltage from 74 v to 20 v and increased the current density from 0.10 to 0.80 amp/cm$^2$. It has been found that increasing the electrolyte concentration increases the metal ion concentration in the aqueous phase. This is illustrated in FIG. 2 which shows how, in the preparation of cobalt octoate, increasing the concentration of tetraethylammonium chloride directly increases the concentration of cobalt ion in the aqueous phase.

Figure 3:
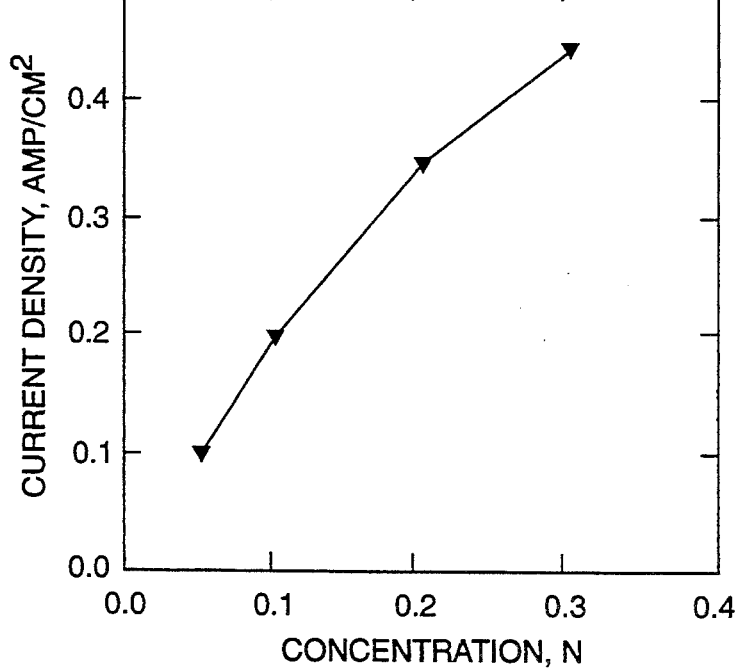
FIG. 3 is a graph showing the relationship between current density and electrolyte concentration.
Figure 4:
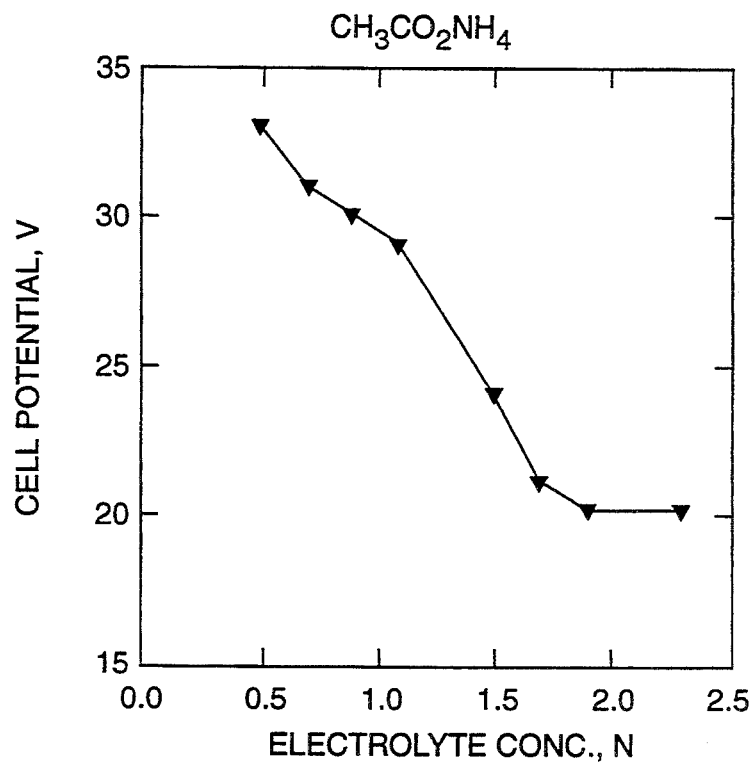
FIG. 4 is a graph showing the relationship between cell potential and electrolyte concentration.
Figure 5:
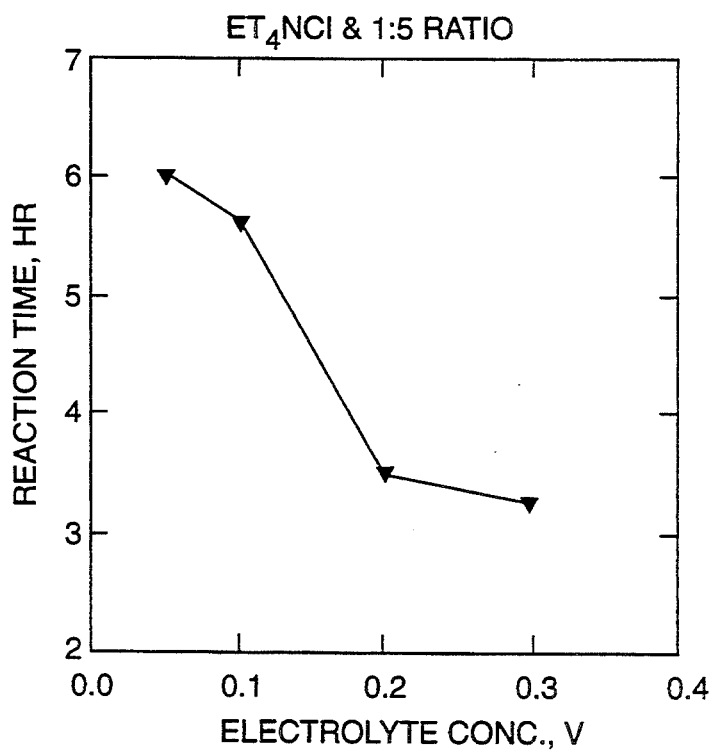
FIG. 5 is a graph showing the relationship between electrolyte concentration and reaction time for equivalent product concentration.

Sodium chloride and ammonium acetate are acceptable electrolyte materials because of their relatively low cost and high conductivity. Increasing the electrolyte concentration generally increases the current density and lowers the required cell voltage and overall reaction time. FIG. 3 shows how, in the preparation of cobalt octoate, the current density increases with an increase in electrolyte concentration. In the preparation of cobalt octoate, the reaction time was reduced to about 3 hours at 1.0N ammonium acetate, and at a cell voltage of less than 20 volts. FIG. 4 shows the inverse relationship between cell potential and electrolyte concentration, and FIG. 5 shows how increasing electrolyte concentration decreased reaction time. Increasing the electrolyte concentration beyond 1.5N, however, showed no significant drop in the cell voltage and promoted heavy cathode plating.

Figure 6:
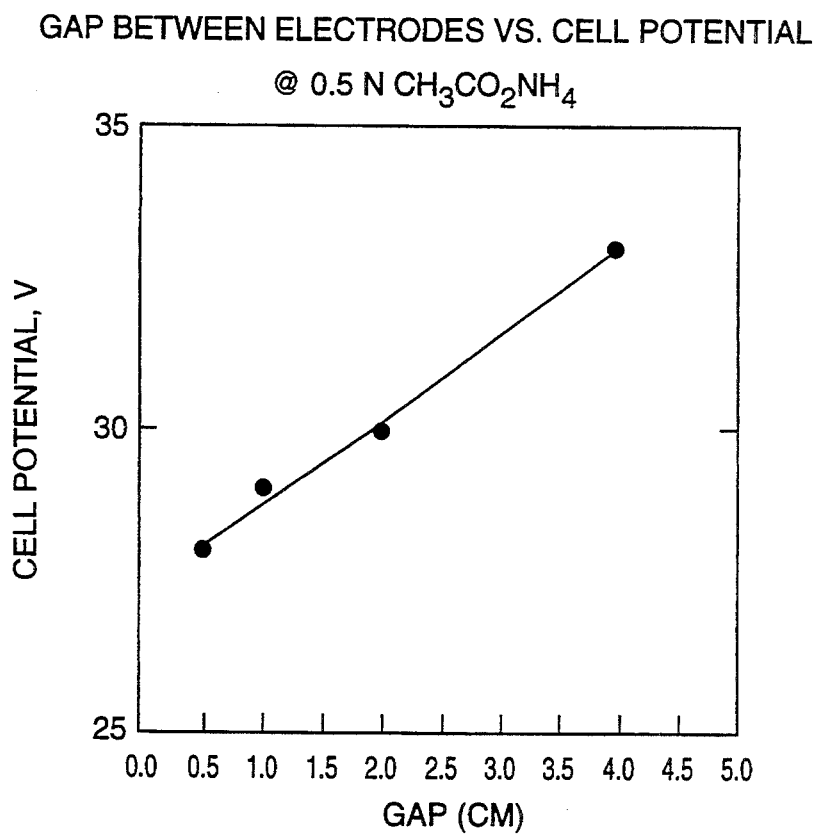
FIG. 6 is a graph illustrating the relationship between cell potential and electrode gap.

Reducing the gap between electrodes lowers the cell voltage and increases the current flow, but, concurrently, increased cathode plating and metal oxide formation also result. In the preparation of cobalt octoate, reducing the gap between electrodes from 9 cm to 3 cm lowered the required cell voltage from 32 volts to 26 volts and increased the current density from 0.35 to 0.40 Amp/cm$^2$. FIG. 6 illustrates the relationship between cell potential and electrode gap for a gap ranging from 0.5 cm to 4.0 cm.

The overall rate of the electrochemical process is directly proportional to the electrode area at a constant voltage. The active area of the electrode is a function of the flow conditions, the extent of the gas evolution, and the cell geometry.

Electrosynthesis at elevated temperatures is generally to be avoided because the cell design must be modified to account for heat dissipation. Elevated temperatures can also aggravate problems associated with corrosion of process equipment, evaporative losses, chemical decomposition, prolonged start-up times from cold, and also increased power cost for heating. On the other hand, temperatures above ambient have a beneficial effect on the kinetics of all steps in the electrosynthesis process.

Figure 7:
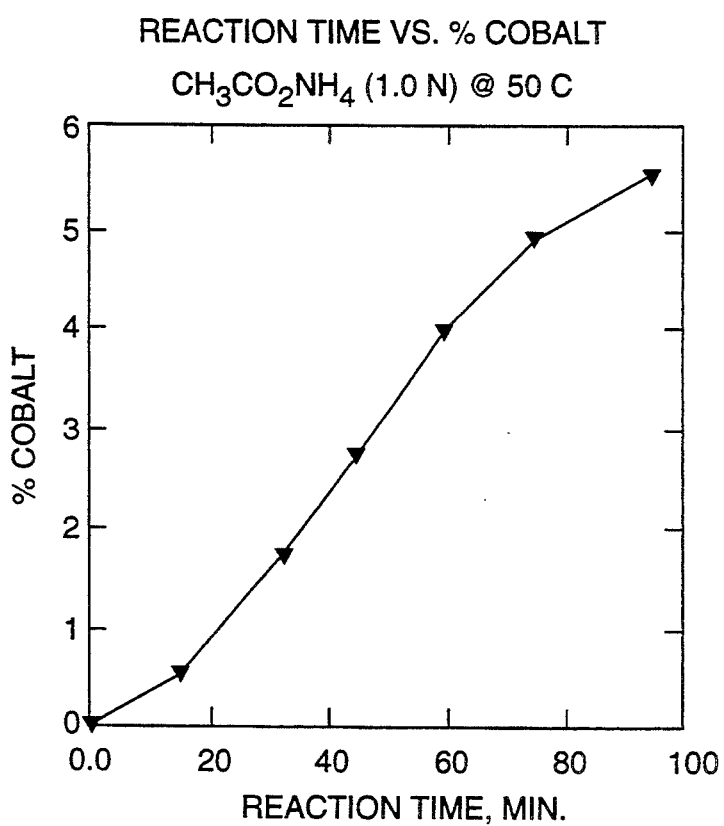
FIG. 7 is a graph showing the rate at which the carboxylate concentration increases during electrosynthesis at a temperature of 50° C.

The temperature of the reaction medium can be varied to determine the optimum range. In the preparation of cobalt octoate, reaction temperatures were varied from ambient to 90° C. The results indicated that increasing the temperature increases the reaction rate but, conversely, heavier cathode plating results. Also, at elevated temperatures, the concentration of the metal in the aqueous phase may increase. In the preparation of cobalt octoate, acceptable results have been obtained at reaction temperatures within the range of 45°–60° C. FIG. 7 shows the rate at which the cobalt concentration increases in the aqueous phase during reaction at a temperature of 50° C.

Turbulence in the electrolytic cell generally increases mass transport of the electroactive species to the electrode surface, promotes the exchange of species between the bulk solution and the boundary layer, and minimizes local pH and other concentration changes due to the electrode reaction. When the electrodes are close together, stirring the reaction mass on a large scale may be a problem because not much room is left for a mechanical agitator.

A possible alternative method would be to circulate the electrolyte past the electrodes by means of an external pump. Another method of homogenizing the reaction mass is moving the electrode itself, such as with a rotating or vibrating electrode.

The emulsion size can be varied to determine whether this parameter can be optimized for a specific system. In the preparation of cobalt octoate, an ultrasonic processor was used to produce a microemulsion. High reaction rates were obtained due to higher current density (1.1 amp/cm$^2$) and lower cell voltage (16 volts). On the other hand, heavier cathode plating resulted and a large amount of metal oxide was formed (10% based on the weight of cobalt octoate).

In the preparation of the metal carboxylate, the ratio of organics/electrolyte should be optimized. In the preparation of cobalt octoate, the ratio was varied between the range of 1:5 to 2:1 by weight organics/electrolyte. The ratio of 1:5 should be considered uneconomical because of the low space yield it would provide. Space yield relates to the amount of product that can be produced in a cell. The space yield improved significantly at a 2:1 ratio, but a higher electrolyte concentration was needed and difficulty in separating the organic and aqueous phases has been noticed. Acceptable results have been obtained at a 1:1 ratio which allows relatively low electrolyte concentrations, and acceptable space yield and phase separation.

Table 1 illustrates the effect of varying several parameters in the preparation of cobalt octoate. The table shows the effect of varying electrolyte type, electrolyte concentration, electrode gap, reaction temperature and organics/electrolyte ratio on cell voltage, current density, reaction time and % metal found in product.

In the method of the invention, the form or geometry of the anode may be varied to optimize reaction conditions. Use of cobalt chips in the preparation of cobalt octoate may offer a cost savings over the use of cobalt foil. An attempt was made to synthesize cobalt octoate electrochemically using cobalt chips in a titanium mesh (20 mesh/linear inch) basket as a carrier for the chips. The basket was used as the anode and a direct current was passed between the two electrodes. Cobalt octoate containing 10% Co has been synthesized with no titanium contamination (<2 ppm Ti) in the product. After a few runs, however, the basket deteriorated and broke.

Another attempt was made using an aluminum basket as a carrier. Cobalt octoate containing 8% Co was prepared, but with some aluminum contamination (850 ppm Al) in the product and the aluminum basket also deteriorated after a while. A plastic mesh basket was then used as a carrier for the chips. Conductivity was established by placing a number of conductive wires in contact with the cobalt chips. Cobalt octoate was also synthesized; however, the current efficiency was lower in this case due to indirect contact between the chips and the electric wires.

In one embodiment of the invention, the metal carboxylate forms a solid which precipitates out of the emulsion. In another embodiment, the metal carboxylate is selectively extracted into the organic phase. This is particularly advantageous in that it provides a direct, convenient means of separating the metal carboxylate from the emulsion. The metal carboxylate is removed from the emulsion by simply separating the organic phase. The metal carboxylate can be extracted from the organic phase, if desired, by any suitable technique including separation of the organic layer from the reaction mixture followed by drying under reduced pressure or filtration and drying of the precipitated metal carboxylate.

In the preparation of cobalt octoate, the extraction of the final product involved separating the organic layer from the aqueous electrolyte layer, followed by filtration of the organic phase to remove any insolubles which can deposit on the cathode or may fall from the anode during the electrosynthesis reaction. The organic layer was then dried on a steam bath at reduced pressure. The filtration step may be eliminated by modifying the electrolytic cell. Installation of a mesh screen in the cell to catch the insolubles before discharging the reaction mixture into a phase separator may also be advisable. With reference to FIG. 1, the mesh screen 17 (illustrated by the dashed lines) can retain the insolubles while the reaction mixture is discharged through conduit 19.

In the electrosynthesis of the metal carboxylate, some soluble metal species may remain in the aqueous electrolyte. The presence of such metal species adds an extra cost to the process due to losses of metal. The soluble metal may be substantially removed from the electrolyte through a subsequent electrolytic process. In the case of cobalt retained in the electrolyte after the preparation of cobalt octoate, the process involved passing a direct current between two graphite electrodes immersed in a stirred mixture of acid/mineral spirits and the electrolyte containing the soluble cobalt species. The process parameters included an applied voltage of 18-80 V and a current density of 0.05-1.0 amp/cm$^2$. The organic layer was then separated from the aqueous layer and both layers were analyzed for their cobalt content. The analyses indicated 78% recovery of cobalt in the organic layer which can be recycled as feedstock for the electrosynthesis of cobalt octoate, while 2% cobalt remained in the aqueous electrolyte with 20% deposited on the cathode.

In the preparation of the metal carboxylate, certain by-products, such as oxides of the metal, may also form. The electrosynthesis of cobalt octoate, for instance, is usually accompanied by the formation of a small amount of cobalt hydroxide and cobalt oxide which can be removed by filtration of the product. In the preparation of cobalt octoate according to the present invention, however, the percentage of cobalt oxide and hydroxide was less than 2% based on the weight of cobalt octoate. It has been found that the formation of metal oxide and hydroxide are influenced by the current density and the electrolyte concentration. In one embodiment, the current density is at least 0.05 amp/cm$^2$. Increasing the current density beyond 1.0 amp/cm$^2$ and the electrolyte concentration beyond 1.5N can result in up to 10% metal oxide and hydroxide, based on the weight of the metal carboxylate. On the other hand, at a current density of 0.8 amp/cm$^2$ and an electrolyte concentration of less than 1.0N, the resulting metal oxide and hydroxide is less than 2%.

Figure 1A:
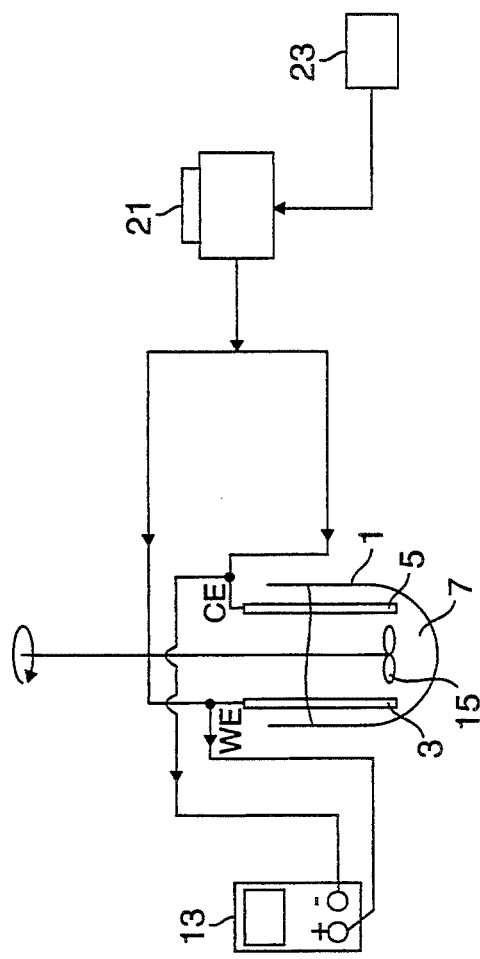
FIG. 1A is a diagram of the arrangement of FIG. 1 modified to apply an AC current.

The cell illustrated in FIG. 1 is an un-divided cell. A divided cell, however, with an anion exchange membrane can be used to prevent the metallic ionic species from reaching the cathode. A divided cell of this type may result in the deposit of the metallic species at the membrane surface. In addition to a divided cell, a gas diffusion electrode may also be used. Such an electrode will allow the passage of current through the cell without allowing plating to occur on the cathode. Another method for preventing plating on the cathode is the application of an AC current. FIG. 1A illustrates the arrangement of FIG. 1 modified to accomodate the application of an AC current. The AC power source 23 communicates with voltage regulator 21 which supplies the electrodes with the AC current. The use of an AC current, however, results in a longer reaction time, and a cooling system must be considered when the cell is designed due to much higher heat generation for comparable product concentration.

A variety of metal carboxylates have been prepared using the method of the present invention. The method has allowed the synthesis of metal carboxylates that: 1) are higher in metal content than that achieved by conventional methods, 2) cannot be made using conventional methods, 3) are cleaner reactions, 4) use less expensive forms of the metal as starting material, and 5) are projected to be less expensive to manufacture than those produced according to conventional techniques.

At least twenty-two (22) metal carboxylates have been synthesized using the process of the invention, with metal concentrations ranging from 5 to 45 wt%. The concentrations were determined using inductively coupled plasma-atomic emission spectroscopy after calibration of the spectrometer with commercially available reference standards. Analyses showed cleaner products than those produced using the conventional thermal batch processes. A number of metal carboxylates synthesized via this technique cannot be synthesized using the conventional thermal bath processes, including titanium octoate, molybdenum octoate, silver neodecanoate and cobalt/vanadium octoate.

The following examples are illustrative of the invention:

EXAMPLE I

Cobalt Octoate

The electrochemical reaction was carried out in a reaction cell containing 20.0 g (0.138 mole) of 2-ethylhexanoic acid, 10.0 g mineral spirits and 40.0 g of 0.1N sodium hydroxide. A cobalt rod was used as the anode and platinum foil as the cathode. The connections were made and direct current was passed through the cell. After passing 14,645 coulombs of electricity, the electrosynthesis process was terminated and the weight of the cobalt consumed in the reaction was determined. 3.68 g (0.062 mole) cobalt was consumed. The organics were separated from the aqueous phase and were dried under reduced pressure resulting in a violet solution of cobalt octoate in mineral spirits that contained 10.1% cobalt.

EXAMPLE II

Cobalt Naphthenate

To a reaction cell equipped with a mechanical stirrer and thermometer was charged 20.0 g (0.107 mole) of naphthenic acid, 10.0 g mineral spirits and 40.0 g of 0.1N sodium hydroxide. A cobalt rod was used as the anode and platinum foil as the cathode. After passing 13,469 coulombs of electricity, 2.47 g (0.419 mole) of cobalt was consumed.

The process was terminated and the reaction product was worked up as described in example I. A dark reddish solution of cobalt naphthenate in mineral spirits was obtained which contained 6.2% cobalt.

EXAMPLE III

Cobalt Acetate

To a reaction flask equipped with a mechanical stirrer and thermometer was charged 9.50 g (0.158 mole) of acetic acid, 9.0 g of mineral spirits and 40 g of 0.1N sodium hydroxide. Cobalt foil was used as the anode and a graphite rod as the cathode. After passing 14,970 coulombs of electricity, 4.32 g (0.073 mole) of cobalt was consumed. The organics were isolated and were tertiurated with acetone. A solid precipitated out of the solution which was filtered and dried. This gave a violet solid material that contained 31.02% cobalt.

EXAMPLE IV

Copper Octoate

To the same reactor described in the previous examples was charged 25.0 g (0.172 mole) of 2-ethylhexanoic acid, 12.5 g of mineral spirits and 50.0 g of 0.1N sodium hydroxide. A copper rod was used as the anode and a graphite rod as the cathode. 13,960 coulombs of electricity were passed and 3.2 g (0.050 mole) of copper was consumed. The precipitated solid was filtered and dried to give a green solid containing 18.2% copper.

The organic materials were isolated and dried and gave a deep green solution of copper octoate in mineral spirits which contains 6.2% copper.

EXAMPLE V

Copper Naphthenate

The reaction flask was charged with 25.0 g (0.134 mole) of naphthenic acid, 12.5 g of mineral spirits and 50.0 g of 0.1N sodium hydroxide. A copper rod was used as the anode and a graphite rod as the cathode. 14,991 coulombs of electricity were passed and 3.57 g (0.056 mole) of copper was consumed. The reaction product was worked up and resulted in a dark green solution of copper naphthenate in mineral spirits which contained 10% copper.

EXAMPLE VI

Copper Oleate

To the reaction flask was charged 27.64 g (0.100 mole) of oleic acid, 10.0 g of mineral spirits and 80.0 g of 0.1N sodium hydroxide. A copper rod was used as the anode and a graphite rod as the cathode. 6,496 coulombs of electricity were passed and 2.30 g (0.030 mole) of copper was consumed. After isolation of the product, a green solution of copper oleate in mineral spirits containing 6% copper was obtained.

The following seven examples (VII–XIII) were run in a homogenous system rather than an emulsion. The resulting metal carboxylates can be produced in an emulsion, however, in which case the final product will be in a solution of the organic phase (for example, mineral spirits) as described in the other examples.

EXAMPLE VII

Copper Laurate

To A reaction flask was charged 24.0 g (0.120 mole) of lauric acid, 60.0 g methanol and 0.40 g of tetraethylammonium chloride hydrate. Copper foil was used as the anode and a graphite rod as the cathode. The reaction mixture was heated to 50° C. and a direct current was passed between the two electrodes. A bluish solid precipitated out which was removed from the electrode surface periodically. After passing 7,803 coulombs of electricity, 3.1 g (0.049 mole) of copper was consumed. The solid was filtered and dried to give a blue solid containing 13.50% copper.

EXAMPLE VIII

Copper Palmitate

To a reaction flask was charged 20.77 g (0.08 mole) of palmitic acid, 60 g methanol and 0.50 g of tetraethylammonium chloride hydrate. Copper foil was used as the anode and a graphite rod as the cathode. A blue solid precipitated during the reaction which had to be removed from the anode surface. After passing 9,690 coulombs of electricity, 3.77 g (0.05 g mole) of copper was consumed. The solid was then filtered and dried to give a blue solid material of copper palmitate containing 15.1% copper.

EXAMPLE IX

Copper Quinolinolate

To a reaction flask was charged 20.05 g (0.12 mole) of 2,3-pyridinecarboxylic acid, 260 g methanol and 0.50 g of tetraethylammonium chloride hydrate. Copper foil was used as the anode and a graphite rod as the cathode. After passing 5,694 coulombs of electricity, 1.94 g (0.031 moles of copper was consumed. A blue solid material of copper quinolinolate containing 4.9% copper was obtained.

EXAMPLE X

Copper Phthalate

To a reaction flask was charged 19.93 g (0.120 mole) of phthalic acid, 100 g of ethanol and 0.50 g of tetraethylammonium chloride hydrate. Copper foil was used as the anode and a graphite rod as the cathode. After passing 9,964 coulombs of electricity, 3.0 g (0.047 mole) of copper was consumed. The solvent was stripped off at reduced pressure to give a blue solid of copper phthalate containing 25.25% copper.

EXAMPLE XI

Copper Acetate

The same procedure was repeated in this reaction except that 9.0 g (0.150 mole) of acetic acid, 60 g methanol and 0.30 g of tetraethylammonium chloride hydrate were used. Copper foil was used as the anode and a graphite rod as the cathode. After passing 15.984 coulombs of electricity, 4.80 g (0.076 mole) of copper was consumed. The reaction solution was filtered to remove the metallic particles and the solvent was removed at reduced pressure. This gave a blue-greenish solid of copper acetate containing 33.6% copper.

EXAMPLE XII

Aluminum Stearate

To a reaction flask was charged 12.0 g (0.0422 mole) of stearic acid, 220 g methanol and 0.40 g of tetraethylammonium chloride hydrate. Aluminum foil was used as the anode and a graphite rod as the cathode. After passing 2,780 coulombs of electricity, 0.56 g (0.021 mole) of aluminum was consumed. A greyish solid precipitated out during the reaction which was filtered, washed with methanol and dried. This gave a grey solid aluminum stearate containing 4.9% aluminum.

EXAMPLE XIII

Zirconium Octoate

To a reaction flask was charged 20.0 g (0.138 mole) of 2-ethylhexanoic acid, 60.0 g of methanol and 0.30 g of tetraethylammonium chloride hydrate. A zirconium rod was used as the anode and a graphite rod as the cathode. After passing 4,664 coulombs of electricity, 1.31 g (0.014 mole) of zirconium was consumed. The methanol was decanted to leave a black waxy residue which was dissolved in 10.0 g of mineral spirits to give a yellow oil containing 5.8% zirconium. After removing the methanol on a rotary evaporator at reduced pressure, a yellow oil containing 1.0% zirconium was obtained.

EXAMPLE XIV

Titanium Octoate

To a reaction flask equipped with an agitator was charged 15.0 g (0,103 mole) of 2-ethylhexanoic acid, 10.0 g of mineral spirits, 60.0 g of 0.1N sodium hydroxide and 0.30 g of tetraethylammonium chloride. Titanium foil was used as the anode and a graphite rod as the cathode. 13,272 coulombs of direct current was passed and 1.43 g (0.030 mole) of titanium was consumed. A white solid precipitated out during the reaction which was filtered and dried. This resulted in a white solid containing 44.6% titanium. The organic layer was separated and produced a white milky oil containing 2.20% titanium.

EXAMPLE XV

Vanadium Octoate

To a reaction flask equipped with an agitator and thermometer was charged 8.0 g (0.055 mole) of 2-ethylhexanoic acid, 9.0 g of mineral spirits, 0.40 g of tetraethylammonium chloride and 60.0 g of water. Vanadium foil was used as the anode and a graphite rod as the cathode. 9,159 coulombs of electricity were passed and 1.65 g (0.032 mole) of vanadium was consumed. The work up procedure produced two types of solid containings 36.10 and 3.30% vanadium respectively, and also resulted in a solution of vanadium octoate in mineral spirits containing 2.40% vanadium.

EXAMPLE XVI

Cobalt/Vanadium Octoate

An attempt was made to prepare a mixture of cobalt and vanadium octoate electrochemically. To a reaction flask equipped with an agitator and thermometer was charged 10.0 g (0.069 mole) of 2-ethylhexanoic acid, 10.0 g mineral spirits, 80.0 g water and 0.40 g tetraethylammonium chloride hydrate. Cobalt foil and vanadium foil were used as the anode and a graphite rod as the cathode. After passing 11,646 coulombs of direct current, 1.22 g (0.021 mole) cobalt and 1.0 g (0.020 mole) vanadium were consumed. The reaction mixture was filtered and the organic phase was separated and dried. A brown solution of cobalt/vanadium octoate in mineral spirits was obtained containing 4.4% cobalt and 7.45% vanadium.

EXAMPLE XVII

Molybdenum Octoate

To a reaction flask equipped with a mechanical stirrer and thermometer was charged 10.0 g (0.069 mole) of 2-ethylhexanoic acid, 10.0 g mineral spirits, 80.0 g water and 0.40 g tetraethylammonium chloride. Molybdenum foil was used as the anode and a graphite rod as the cathode. After passing 14,125 coulombs of direct current, 2.45 g (0.026 mole) of molybdenum was consumed. The mineral spirits layer was clear and the product stayed in the aqueous phase. The water was removed on a rotary evaporator under reduced pressure and gave a deep blue solid containing 21.8% molybdenum.

EXAMPLE XVIII

Iron Octoate

To a reaction flask equipped with a mechanical agitator and thermometer was charged 10.0 g (0,069 mole) of 2-ethylhexanoic acid, 10.0 g mineral spirit, 80.0 g water and 0.40 g tetraethylammonium chloride. Iron foil was used as the anode and a graphite rod as the cathode. After passing 11,109 coulombs of direct current, 3.43 g (0,061 mole) of iron was consumed. The precipitated brown solid was then filtered and dried, and found to contain 45.60% iron. The organic layer was separated from the aqueous phase and was dried to give a brown solution of iron octoate in mineral spirits containing 14.10% iron.

EXAMPLE XIX

Nickel Octoate

To a reaction flask equipped with a mechanical stirrer and thermometer was charged 10.0 g (0,069 mole) of 2-ethylhexanoic acid, 10.0 g mineral spirits, 80.0 g water and 0.45 g of tetraethylammonium chloride. The electrical connections were then made and 11,416 coulombs of direct current were passed. 3.30 g (0,056 mole) of nickel was consumed. After removal of the aqueous layer, a greenish semi-solid was obtained. This material was tertiurated with acetone and gave a green solid containing 7.30% nickel. The filtrate was dried and the acetone was stripped off on a rotary evaporator under reduced pressure. This resulted in a green solution of nickel octoate in mineral spirits containing 10.9% nickel.

EXAMPLE XX

Silver Neodecanoate

To a reaction flask equipped with a mechanical stirrer, thermometer was charged 12.0 g (0.070 mole) of neodecanoic acid, 60 g of 0.1N sodium hydroxide. Silver foil was used as the anode and a graphite rod as the cathode. After passing 5,590 coulombs of direct current, 3.47 g (0.032 mole) of silver was consumed. A black sticky material was obtained after removal of the aqueous phase. This material was tertiurated with acetone and gave a black crystalline solid containing 25.0% silver. From the acetone was obtained a white solid containing 28.0% silver.

EXAMPLE XXI

Copper Gluconate

To a reaction flask equipped with a mechanical stirrer and thermometer was charged 40.0 g (0.102 mole) of 50% solution of a gluconic acid and 40.0 g (0.3N) of sodium hydroxide. Copper foil was used as the anode and a graphite rod as the cathode. After passing 5,899 coulombs of electricity, 7.15 g (0.113 mole) of copper was consumed.

The reaction solution was filtered to remove the copper particles, then methanol was added to it. A solid precipitated out which was filtered and dried to give a green solid containing 19.46% copper.

Table 2 illustrates the percent yields and current efficiency for the preparation of the materials described in the examples.

TABLE 1

ELECTROSYNTHESIS OF COBALT OCTOATE

| Electrolyte Type | Electrolyte Conc., N | Reaction Time, hr/ Temp. °C. | Cell Voltage V | Current Density Amp. cm$^2$ | Gap cm | Ratio of Organics/ Electrolyte | % Metal in Product Found/Calc. |
|---|---|---|---|---|---|---|---|
| Et$_4$NCl | 0.05 | 6/45 | 35 | 0.10 | 6 | 1:5 | 20.10/10.20 |
| Et$_4$NCl | 0.10 | 5.6/45 | 33 | 0.20 | 6 | 1:5 | 10.70/10.90 |
| Et$_4$NCl | 0.20 | 4.00/45 | 30 | .35 | 6 | 1:5 | 8.80/9.30 |
| Et$_4$NCl | 0.30 | 3.25/45 | 28 | 0.45 | 6 | 1:5 | 8.80/9.10 |
| Et$_4$NI | 0.10 | 8.5/45 | 35 | 0.10 | 6 | 1:5 | 7.9/7.90 |
| NaCl | 0.20 | 3.25/45 | 31 | 0.53 | 6 | 1:5 | 10.90/10.00 |
| NH$_4$Cl | 0.20 | 4.50/45 | 32 | 0.30 | 6 | 1:5 | 10.20/10.00 |
| CH$_3$CO$_2$NH$_4$ | 0.20 | 4.00/45 | 29 | 0.40 | 6 | 1:5 | 11.70/10.00 |
| NaCl | 0.60 | 4.00/45 | 32 | 0.35 | 9 | 1:1 | 10.00/10.00 |
| NaCl | 0.60 | 3.00/45 | 26 | 0.40 | 3 | 1:1 | 11.60/10.00 |
| NaCl | 1.00 | 3.50/45 | 26 | 0.80 | 3 | 2:1 | 8.20/7.00 |
| NaCl | 1.50 | 3.00/70 | 25 | 0.80 | 3 | 2:1 | 15.70/12.90 |
| NaCl | 1.50 | 3.50/70 | 28 | 0.80 | 6 | 2:1 | 10.20/10.00 |
| CH$_3$CO$_2$NH$_4$ | 0.40 | 3.50/90 | 28 | — | 3 | 1:1 | 8.50/7.90 |
| CH$_3$CO$_2$NH$_4$[1] | 1.00 | 5.50/45 | 28 | — | 3 | 1:1 | 10.10/9.40 |
| CH$_3$CO$_2$NH$_4$[2] | 1.00 | 5.00/45 | 26 | — | 0.50 | 1:1 | 10.2/10.00 |
| CH$_3$CO$_2$NH$_4$[3] | 1.00 | 8.00/60 | 26 | — | 3 | 1:1 | 7.3/8.00 |

[1] A titanium basket anode was used.
[2] An aluminum basket anode was used.
[3] A plastic basket anode was used.

TABLE 2

ELECTROSYNTHESIS OF METAL CARBOXYLATES

| Compound | Theory | Found | Current Efficiency, % | Form | Color | Process |
|---|---|---|---|---|---|---|
| Co Octoate | 10.9 | 10.1 | 83 | Sol. in min. sp. | Violet | Emulsion |
| Co Naphthenate | 7.2 | 6.2 | 61 | Sol. in min. sp. | Red Violet | Emulsion |
| Cu Octoate | 8.7 | 6.2,13.5 | 90 | Solid | Green Blue | Emulsion |
| Cu Naphthenate | 10.0 | 10.0 | 93 | Sol'n in min. sp. | Deep Green | Emulsion min. sp. |
| Cu Oleate | 6.1 | 6.5 | 100 | Sol'n in min. sp. | Green | Emulsion |

TABLE 2-continued
ELECTROSYNTHESIS OF METAL CARBOXYLATES

| Compound | Theory | Found | Current Efficiency, % | Form | Color | Process |
|---|---|---|---|---|---|---|
| Cu Laurate | 13.7 | 13.5 | 99 | Solid | Blue | Methanol |
| Cu Palmitate | 10.9 | 15.1 | 100 | Solid | Blue | Methanol |
| Cu Quinolinolate | 5.2 | 4.9 | 59 | Solid | Violet | Methanol |
| cu Phthalate | 16.1 | 25.3 | 50 | Solid | Blue | Methanol |
| Co Acetate | 33.29 | 31.0 | 94 | Solid | Violet | Methanol |
| Cu Acetate | 34.98 | 33.50 | 65 | Solid | Green | Methanol |
| Zr Octoate | 5.30 | 5.8 | 52 | Sol'n in min. sp. | Yellow | Methanol |
| Al Stearate | 4.50 | 4.80 | 100 | Solid | Grey | Methanol |
| Ti Octoate | 4.90 | 2.20,44.50 | 50 | solid | White | Emulsion |
| V Octoate | 8.10 | 8.10 | 69 | Solid | Dk Green | Emulsion |
| Co/V Octoate | 5.4 Co 5.8 V | 4.40 Co 7.40 V | 85 | Sol'n in min. sp. | Brown | Emulsion |
| Mo Octoate | 25.0 | 21.80 | 51 | Solid | Dk Blue | Emulsion |
| Fe Octoate | 14.6 | 45.60,14.1 | 100 | Solid | Brown | Emulsion |
| Ni Octoate | 14.20 | 7.30 10.9 | 100 | Solid Sol'n in min. sp. | Green | Emulsion |
| Ag Neodecanoate | 24.0 | 25.0 | 100 | Solid | Grey-black White | Neat |
| Cu Gluconate | 14.0 | 19.50 | 90 | Solid | Green | Neat |
| Au Octoate | | | | Solid | Brown | Methanol |

Note: Current efficiencies are based on metal consumed in the process and metal content in the product.

What is claimed is:

1. A method of synthesizing a metal carboxylate comprising:

placing an anode and a cathode in contact with an emulsion, wherein said anode comprises a metal or metal alloy which includes cobalt, copper, zirconium, aluminum, titanium, vanadium, iron, molybdenum, nickel, silver, or gold, said cathode comprises a material selected from the group consisting of platinum, stainless steel and graphite, and said emulsion comprises a carboxylic acid selected from the group consisting of 2-ethylhexanoic, naphthenic, oleic, lauric, palmitic, phthalic, acetic, gluconic, neodecanoic acids, and mixtures thereof, an aqueous phase containing an electrolyte selected from the group consisting of sodium hydroxide, tetraethylammonium chloride, tetraethylammonium iodide, sodium chloride, tetrabutylammonium perchlorate, tetraethylammonium bromide, tetraethylammonium p-toluene sulfonate, ammonium acetate, and mixtures thereof, at a concentration within the range of 0.02 to 1.5N, and an organic phase selected from the group consisting of mineral spirits, heptane, hexane, petroleum ether, and mixtures thereof; and, passing a current between the anode and cathode to effect electrolytic reaction between the metal of the anode and the carboxylic acid to form the metal carboxylate.

2. The method of claim 1 wherein the weight ratio of organic phase to electrolyte is within the range of 1:5 to 2:1.

3. The method of claim 1 wherein a voltage within the range of 18 to 80 volts is applied when passing the current between the anode and cathode.

4. The method of claim 1 wherein a current density within the range of 0.05 to 1.0 amp/cm$^2$ is maintained when passing the current between the anode and cathode.

5. The method of claim 4 wherein the electrolyte concentration in the aqueous phase is less than 1.0N and the current density is at least 0.05 amp/cm$^2$.

6. The method of claim 1 wherein an AC current is passed between the anode and the cathode.

7. The method of claim 1 wherein a DC current is passed between the anode and the cathode.

8. The method of claim 1 wherein the organic phase comprises mineral spirits.

9. A method of synthesizing a metal carboxylate comprising:

placing an anode and a cathode in contact with an emulsion, wherein said anode includes a metal which, during electrolysis, reacts with a carboxylic acid to form a metal carboxylate, said cathode comprises a material inert to the electrolytic reaction, and said emulsion comprises a carboxylic acid, an aqueous phase which includes an electrolyte, and an organic phase; and, passing a current between said anode and cathode to effect an electrolytic reaction between the metal of the anode and the carboxylic acid to form the metal carboxylate, wherein said metal carboxylate is selectively extracted into the organic phase.

10. The method of claim 9 wherein the organic phase comprises mineral spirits.

11. The method of claim 10 wherein the electrolyte comprises sodium hydroxide.

12. The method of claim 9 wherein the anode comprises copper or cobalt and the cathode comprises graphite.

13. The method of claim 12 wherein the anode comprises copper foil.

14. The method of claim 9 wherein the carboxylic acid comprises 2-ethylhexanoic acid.

15. The method of claim 9 wherein mechanical stirring means are used to stir the emulsion as the current is passed between the anode and cathode.

16. The method of claim 9 wherein a temperature within the range of 45° C. to 60° C. is maintained in the emulsion when passing the current between the anode and the cathode.

17. A method of forming a metal octoate comprising:
placing an anode and a cathode in contact with an emulsion, wherein said anode comprises a metal selected from the group consisting of cobalt, copper, nickel, iron, vanadium, molybdenum, titanium, and zirconium, said cathode comprises an electrolytically inert material, and said emulsion comprises 2-ethylhexanoic acid, an aqueous phase which includes an electrolyte, and an organic phase; and, passing a current between said anode and cathode to effect an electrolytic reaction between the metal of the anode and the 2-ethylhexanoic acid to form the metal octoate.

18. The method of claim 17 wherein a voltage in the range of 18 to 80 volts and a current density in the range of 0.05 to 1.0 amps/cm$^2$ are maintained when passing the current between the anode and the cathode.

19. The method of claim 17 wherein the concentration of the electrolyte is within the range of 0.02N to 1.5N.

20. The method of claim 17 wherein the electrolyte comprises sodium hydroxide and the organic phase comprises mineral spirits.

* * * * *

UNITED STATES PATENT AND TRADEMARK OFFICE
CERTIFICATE OF CORRECTION

PATENT NO. : 5,443,698

DATED : August 22, 1995

INVENTOR(S) : Mahoney et al.

It is certified that error appears in the above-identified patent and that said Letters Patent is hereby corrected as shown below:

Column 11, Example XVIII, line 10, "(0,061 mole)" should be (0.061 mole)";

Column 11, Example XIX, line 24 "(0,056 mole)" should be "(0.056 mole)";

Table 1, first line, last column "20.10/10.20" should be "10.10/10.20".

Signed and Sealed this

Ninth Day of January, 1996

Attest:

BRUCE LEHMAN

Attesting Officer    Commissioner of Patents and Trademarks